(12) United States Patent
Waksal

(10) Patent No.: US 10,080,752 B2
(45) Date of Patent: Sep. 25, 2018

(54) TREATMENT OF BRAIN AND CENTRAL NERVOUS SYSTEM TUMORS

(71) Applicant: KADMON CORPORATION LLC, New York, NY (US)

(72) Inventor: Samuel Waksal, New York, NY (US)

(73) Assignee: KADMON CORPORATION, LLC, New York, NY (US)

( * ) Notice: Subject to any disclaimer, the term of this patent is extended or adjusted under 35 U.S.C. 154(b) by 0 days.

(21) Appl. No.: 15/125,303

(22) PCT Filed: Mar. 10, 2015

(86) PCT No.: PCT/US2015/019658
§ 371 (c)(1),
(2) Date: Sep. 12, 2016

(87) PCT Pub. No.: WO2015/138420
PCT Pub. Date: Sep. 17, 2015

(65) Prior Publication Data
US 2017/0071943 A1    Mar. 16, 2017

Related U.S. Application Data

(60) Provisional application No. 61/950,707, filed on Mar. 10, 2014.

(51) Int. Cl.
*A61K 31/517* (2006.01)
*A61K 45/06* (2006.01)
*A61K 31/495* (2006.01)
*C07D 403/12* (2006.01)

(52) U.S. Cl.
CPC .......... *A61K 31/517* (2013.01); *A61K 31/495* (2013.01); *A61K 45/06* (2013.01); *C07D 403/12* (2013.01)

(58) Field of Classification Search
CPC .................................................. A61K 31/517
See application file for complete search history.

(56) References Cited

U.S. PATENT DOCUMENTS

2009/0318373 A1* 12/2009 Rice ..................... C07D 239/94
514/25

FOREIGN PATENT DOCUMENTS

WO    2008/094484 A2    8/2008
WO    2010/085845 A1    8/2010
WO    2013/101964 A1    7/2013

OTHER PUBLICATIONS

Chi, A. et al., "Treatment of Brain Metastasis from Lung Cancer", Cancers (2010); vol. 2:4; pp. 2100-2137.
Ramis, G. et al., "EGFR Inhibition in Glioma Cells Modulates Rho Signaling to Inhibit Cell Motility and Invasion and Cooperates with Temozolomide to Reduce Cell Growth"; Plos One (2012); vol. 7:6; pp. e38770 14 pgs.
Extended Search Report dated Aug. 25, 2017 from related European Application No. 157 607 94.6; 10 pgs.

* cited by examiner

*Primary Examiner* — Paul V Ward
(74) *Attorney, Agent, or Firm* — Fox Rothschild LLP

(57) ABSTRACT

The present invention provides methods for treating tumors of the brain by administering the compounds of the Formula A and particularly N-(3,4-dichloro-2-fluorophenyl)-7-({[(3aR,6aS)-2-methyloctahydrocyclopenta[c]pyrrol-5-yl]methyl}oxy)-6-(methyloxy)quinazolin-4-amine, or a pharmaceutically acceptable salt thereof, to a subject in need of such treatment. In the methods of the invention, the compounds disclosed herein were surprisingly found to cross the blood brain barrier. The method of the present invention further relates to the treatment of cancers of any type potentially responding to EGFR, HER2, VEGFR2, or Src family kinase inhibitors and that are found in the brain.

2 Claims, 2 Drawing Sheets

TREATMENT OF BRAIN AND CENTRAL NERVOUS SYSTEM TUMORS

CROSS REFERENCE TO RELATED APPLICATIONS

This application is a 371 of International Patent Application No. PCT/US2015/019658, filed Mar. 10, 2015, which claims priority to U.S. Provisional Patent Application Ser. No. 61/950,707, filed Mar. 10, 2014. The contents of these applications are hereby incorporated by reference in their entireties.

FIELD OF THE INVENTION

The present invention concerns methods for treating tumors of the brain by administering the compound N-(3,4-dichloro-2-fluorophenyl)-7-({[(3aR,6aS)-2-methyloctahydrocyclopenta[c]pyrrol-5-yl]methyl}oxy)-6-(methyloxy)quinazolin-4-amine, or a pharmaceutically acceptable salt thereof, to a subject in need of such treatment. The method of the present invention further relates to the treatment of cancers of any type potentially responding to EGFR, HER2, VEGFR2, or Src family kinase inhibitors that are growing in the brain. The present invention further provides combination therapies with radiation and/or temozolomide.

BACKGROUND

Brain and central nervous system tumors are often particularly difficult to treat. They may originate in the central nervous system (CNS) as primary tumors, or they may be metastases from tumors which arise in other organs or tissues. The most common types of primary tumor of the brain and CNS are malignant gliomas, which can spread aggressively and often diffusely into normal brain tissue.

Chemotherapy-based treatment of brain and central nervous system tumors is frequently ineffective, particularly in the case of metastases from non-primary tumors, which are often drug resistant. Furthermore, the blood brain barrier (BBB) presents a challenge to treatment by preventing access of therapeutic drugs to the tumor. As a result, the mean survival time for patients with metastases from small-cell lung cancer, breast cancer, and melanoma can be depressingly short. The addition of whole-brain radiation therapy can provide some added benefit, but such benefit is often minimal.

SUMMARY OF THE INVENTION

It has been discovered that compounds of formula A cross the blood brain barrier, and are useful to treat tumors and neoplasms of the brain and central nervous system (CNS):

Formula A

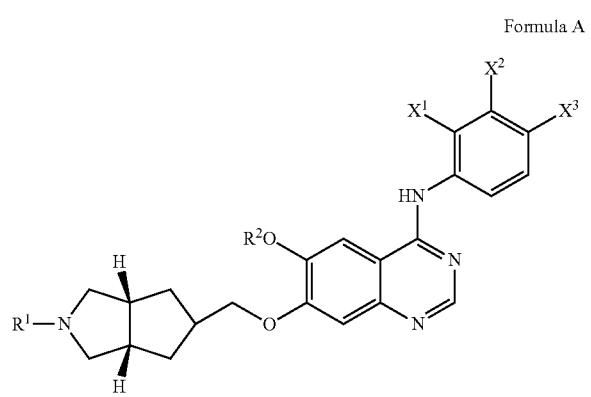

wherein
each of $X^1$, $X^2$ and $X^3$ are independently selected from the group consisting of H, F and Cl, wherein at least two of $X^1$, $X^2$ and $X^3$ are F or Cl;
$R^1$ is $C_1$ to $C_3$ alkyl; and $R^2$ is $C_1$ to $C_3$ alkyl;
or a pharmaceutically acceptable salt thereof.

In a preferred embodiment of the invention, a compound of Formula 1 crosses the blood brain barrier, and is useful to treat tumors and neoplasms of the brain and central nervous system (CNS):

Formula 1

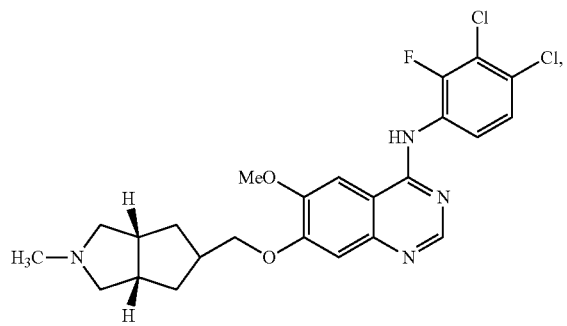

The present invention provides a method of treating a brain or central nervous system tumor comprising administering to a subject in need of such treatment a therapeutically effective amount of a compound of Formula A, or a pharmaceutically acceptable salt thereof.

In certain embodiments of the present invention, the compound of Formula A is N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine or N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine (Formula 1). In another embodiment of the present invention, the pharmaceutically acceptable salt is the salt of p-toluenesulfonic acid.

In certain embodiments of the present invention, a brain or CNS tumor is treated by administering a compound of Formula 1 and administering a chemotherapeutic agent such as temozolomide and/or administering radiation.

In some embodiments of the present invention, the subject is human and the brain or CNS tumor has not been previously treated. In other embodiments of the present invention, the subject is human and the brain or CNS tumor has previously been treated with temozolomide.

DETAILED DESCRIPTION OF THE INVENTION

Figure 1:
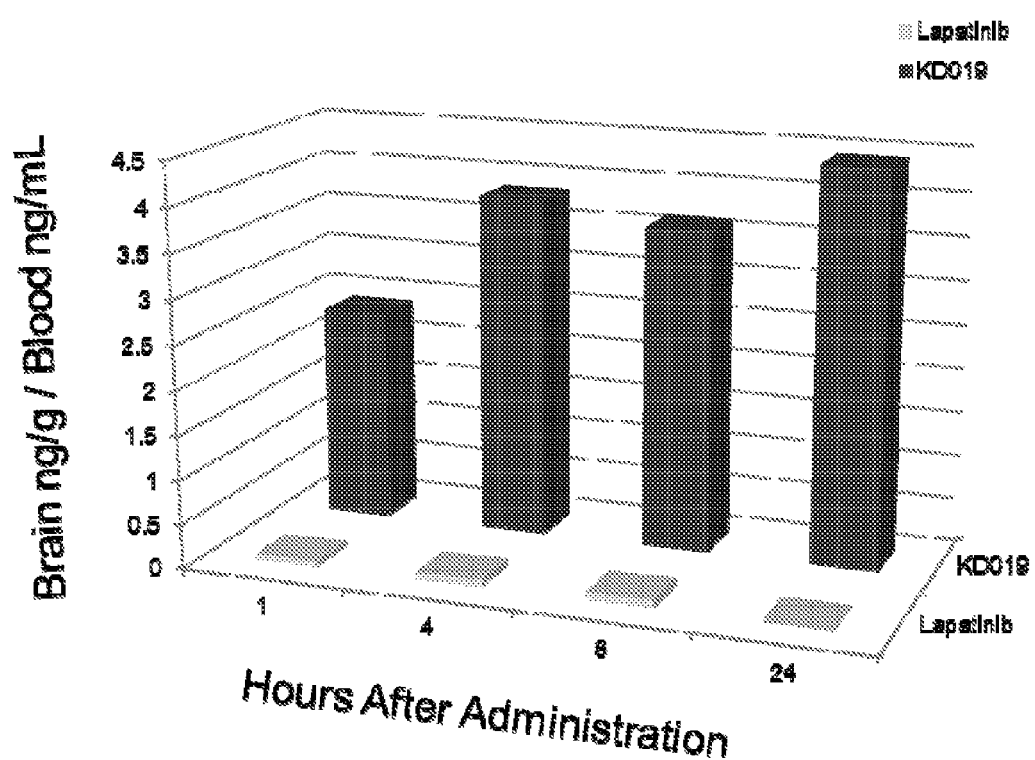
FIG. 1 shows the ratio of N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine in the CNS compared to the amount in circulating blood up to 24 hours after administration. The tissue distribution is compared to lapatinib, which does not cross the blood-brain barrier (BBB).

Provided herein are methods of treating a brain or central nervous system tumor comprising administering to a subject in need of such treatment a therapeutically effective amount of a compound of Formula A:

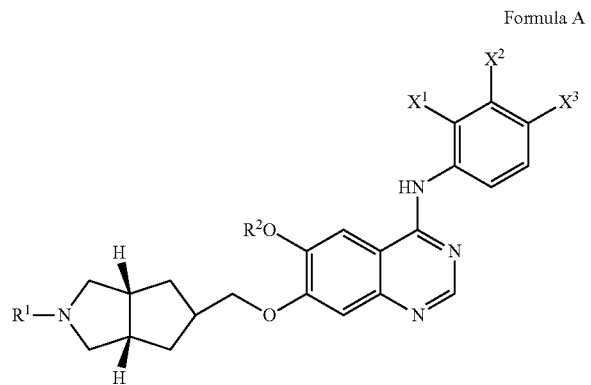

Formula A wherein
each of $X^1$, $X^2$ and $X^3$ are independently selected from the group consisting of H, F and Cl, wherein at least two of $X^1$, $X^2$ and $X^3$ are F or Cl;
$R^1$ is $C_1$ to $C_3$ alkyl; and $R^2$ is $C_1$ to $C_3$ alkyl;
or a pharmaceutically acceptable salt thereof.

In preferred embodiments the compound of Formula A is a compound having the Formula 1:

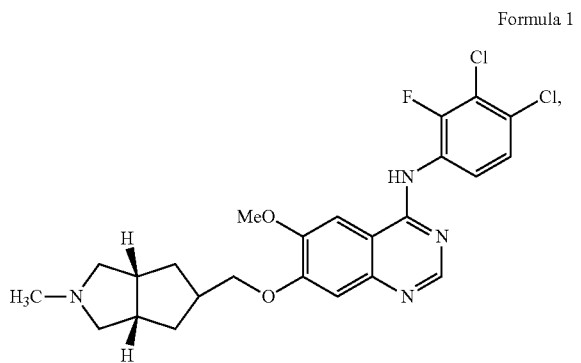 [SMILES: COc1cc2c(Nc3ccc(Cl)c(Cl)c3F)ncnc2cc1OCC1C[C@@H]2CN(C)C[C@@H]2C1]

Formula 1 or a pharmaceutically acceptable salt thereof. The chemical name of the compound of Formula 1 is N-(3,4-dichloro-2-fluorophenyl)-7-({[(3aR,6aS)-2-methyloctahydrocyclopenta[c]pyrrol-5-yl]methyl}oxy)-6-(methyloxy)quinazolin-4-amine. In certain embodiments, the brain or central nervous system tumor does not include glioblastoma.

The compound of Formula A, and its pharmaceutically acceptable salts, includes stereoisomers, enantiomers, diastereomers, racemates, and racemic or non-racemic mixtures thereof, as well as any pharmaceutically acceptable salts of said stereoisomers, enantiomers, diastereomers, racemates and racemic or non-racemic mixtures.

In an embodiment of the invention, the compound of Formula 1 is N-(3,4-dichloro-2-fluorophenyl)-7-({[(3 aR,5r, 6aS)-2-methyloctahydrocyclopenta[c]pyrrol-5-yl]methyl}oxy)-6-(methyloxy)quinazolin-4-amine or N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, or a pharmaceutically acceptable salt thereof. In another embodiment of the invention, the pharmaceutically acceptable salt is the salt of p-toluenesulfonic acid.

As used herein, the term pharmaceutically acceptable salt(s) includes pharmaceutically acceptable acid addition salts. Pharmaceutically acceptable acid addition salts are salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, hexanoic acid, heptanoic acid, cyclopentanepropionic acid, glycolic acid, pyruvic acid, lactic acid, malic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, stearic acid, and the like. A preferred pharmaceutically acceptable acid addition salt is the salt of p-toluenesulfonic acid.

The compound of Formula A and pharmaceutically acceptable salts thereof can be manufactured using techniques commonly known in the art. For example, said compound and pharmaceutically acceptable salts thereof, as well as methods of manufacturing them, are disclosed in U.S. Pat. Nos. 7,576,074 and 8,658,654, which are incorporated herein by reference. U.S. Pat. Nos. 7,576,074 and 8,658,654 were assigned from Exelixis, Inc. to Symphony Evolution, Inc. on Jun. 10, 2009. Kadmon Corporation, LLC has acquired certain rights to the compound of Formula 1 (also known as XL647, EXEL-7647 and KD-019. The compound of Formula A, in addition to being an inhibitor of several receptor tyrosine kinases (RTKs), is also an inhibitor of the SRC kinase.

It has been discovered that the compound of Formula A, and particularly Formula 1, efficiently penetrates the blood brain barrier (BBB). Accordingly, the compound of Formula A is useful for treating, inhibiting, or ameliorating neoplastic diseases of the brain and central nervous system. The method of the present invention provides the treatment of cancers and neoplastic diseases of any type potentially responding to EGFR, HER2, VEGFR2, or Src family kinase inhibitors that are growing in the brain.

In some embodiments, the brain or central nervous system tumor is a primary brain or central nervous system tumor selected from the group consisting of astrocytoma (e.g., pilocystic astrocytoma, anaplastic astrocytoma), oligodendroglioma, ependymoma, polar spongioblastoma, astroblastoma, gliomatosis cerebri, meningioma, medulloblastoma, brain stem glioma, craniopharyngioma, pituitary tumor, primary lymphoma of the brain, pineal gland tumor, primary germ cell tumor of the brain, choroid plexus papilloma, acoustic neuroma, schwannoma, craniopharyngioma, nerve glioma, a primitive neuroectodermal tumor, and rhabdoid tumor. In embodiments where the compound of Formula A, and particularly Formula 1, is administered with a [3H]-imidazo[5,1-d]-1,2,3,5-tetrazin-4-one derivative such as temozolomide, the brain or central nervous system tumor may be a glioblastoma, e.g., glioblastoma multiforme.

In some embodiments, the central nervous system or brain tumor is a metastasized tumor that arose from a tumor outside the central nervous system or brain selected from the group consisting of lung, breast, colon, kidney, prostate, bladder, melanoma, thyroid, germ cell, and uterine tumors.

In a particular embodiment, the brain tumor has metastasized to the brain from a lung tumor.

In some embodiments, the invention provides a method for treating refractory tumors, particularly refractory malignant tumors. Refractory tumors include tumors that fail or are resistant to treatment with chemotherapeutic agents alone, radiation alone or combinations thereof. For the purposes of this specification, refractory tumors also encompass tumors that appear to be inhibited by treatment with chemotherapeutic agents and/or radiation but recur up to five years, sometimes up to ten years or longer after treatment is discontinued.

In some embodiments, the central nervous system or brain tumor is a tumor that is responsive to treatment with trastuzumab. In some embodiments, the central nervous system or brain tumor is a tumor that is responsive to treatment with an intracellular or extracellular HER2 antagonist. In some embodiments, the central nervous system or brain tumor is a tumor that is responsive to treatment with an intracellular or extracellular EGFR antagonist. Responsiveness to an extracellular or intracellular antagonist of EGFR or HER2 includes responsiveness in an in vitro assay, for example for an antagonist that does not cross the BBB.

Furthermore, the compound of Formula A can be used in conjunction with other methods and compositions for treating brain and central nervous system neoplasms and tumors such as, e.g., radiation, targeted small molecules, and/or chemotherapeutic agents.

In some embodiments, provided are methods of treating brain tumors comprising administering to a patient in need thereof a therapeutically effective amount of the compound of Formula A, and particularly Formula 1, and a therapeutically effective amount of a [3H]-imidazo[5,1-d]-1,2,3,5-tetrazin-4-one derivative of the formula

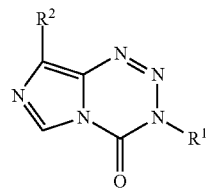

wherein $R^1$ represents hydrogen, or an alkyl, alkenyl or alkynyl group containing from 1 to 6 carbon atoms, or a said group substituted by from one to three substituents selected from halogen atoms, alkoxy, alkylthio, alkylsulphinyl and alkylsulphonyl groups containing up to 4 carbon atoms, and phenyl substituted by alkoxy and alkyl groups containing from 1 to 4 carbon atoms or a nitro group; or $R^1$ represents a cycloalkyl group containing from 3 to 8 carbon atoms, and $R^2$ represents a carbamoyl group, or a carbamoyl group carrying on the nitrogen atom one or two groups selected from alkyl and alkenyl groups containing up to 4 carbon atoms, and cycloalkyl groups containing from 3 to 8 carbon atoms, and—when $R^1$ represents hydrogen—alkali metal salts thereof.

In the [3H]-imidazo[5,1-d]-1,2,3,5-tetrazin-4-one derivatives described above, when the symbol $R^1$ represents an alkyl, alkenyl or alkynyl group substituted by two or three halogen atoms, the aforesaid halogen atoms may be the same or different. When the symbol $R^1$ represents an alkyl, alkenyl or alkynyl group substituted by one, two or three optionally substituted phenyl groups the optional substituents on the phenyl radical(s) may be selected from, for example, alkoxy and alkyl groups containing up to 4 carbon atoms (e.g., methoxy and/or methyl group(s)) and the nitro group; the symbol $R^1$ may represent, for example, a benzyl or p-methoxybenzyl group. Cycloalkyl groups within the definitions of symbols $R^1$ and $R^2$ contain 3 to 8, preferably 6, carbon atoms.

In certain embodiments of the [3H]-imidazo[5,1-d]-1,2,3,5-tetrazin-4-one derivatives described above, $R^1$ represents a straight- or branched-chain alkyl group containing from 1 to 6 carbon atoms optionally substituted by one or two halogen (preferably chlorine, fluorine or bromine) atoms or by an alkoxy group containing 1 to 4 carbon atoms (preferably methoxy) or by a phenyl group (optionally substituted by one or two alkoxy groups containing from 1 to 4 carbon atoms, preferably methoxy), or $R^1$ represents an alkenyl group containing 2 to 6 carbon atoms (preferably allyl) or a cyclohexyl group.

In other embodiments, $R^1$ represents a straight- or branched-chain alkyl group containing from 1 to 6 carbon atoms, and more especially from 1 to 3 carbon atoms, unsubstituted or substituted by a halogen, preferably chlorine or fluorine, atom. More especially $R^1$ represents a methyl or 2-haloalkyl, e.g., 2-fluoroethyl or, preferably, 2-chloroethyl, group.

In some embodiments, $R^2$ represents a carbamoyl group or a monoalkylcarbamoyl, e.g., methylcarbamoyl, or monoalkenylcarbamoyl group.

When $R^1$ represents a hydrogen atom in the [3H]-imidazo[5,1-d]-1,2,3,5-tetrazin-4-one derivatives described above, the derivatives may be in the form of salts, e.g., alkali metal salts such as sodium salts.

In some embodiments, the [3H]-imidazo[5,1-d]-1,2,3,5-tetrazin-4-one derivative described above is 3,4-dihydro-3-methyl-4-oxoimidazo[5,1-d]-as-tetrazine-8-carboxamide (temozolomide)

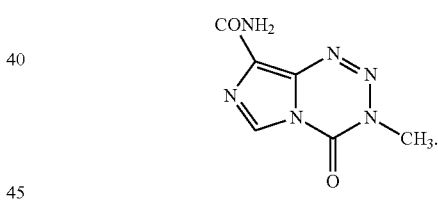

In other embodiments, the [3H]-imidazo[5,1-d]-1,2,3,5-tetrazin-4-one derivative described above is selected from the group consisting of:
  8-carbamoyl-3-n-propyl-[3H]-imidazo[5,1-d]-1,2,3,5-tetrazin-4-one,
  8-carbamoyl-3-(2-chloroethyl)-[3H]-imidazo-[5,1-d]-1,2,3,5-tetrazin-4-one,
  3-(2-chloroethyl)-8-methylcarbamoyl-[3H]-imidazo[5,1-d]-1,2,3,5-tetrazin-4-one,
  8-carbamoyl-3-(3-chloropropyl)-[3H]-imidazo-[5,1-d]-1,2,3,5-tetrazin-4-one,
  8-carbamoyl-3-(2,3-dichloropropyl)-[3H]-imidazo[5,1-d]-1,2,3,5-tetrazin-4-one,
  3-allyl-8-carbamoyl-[3H]-imidazo[5,1-d]-1,2,3,5-tetrazin-4-one,
  3-(2-chloroethyl)-8-dimethylcarbamoyl-[3H]-imidazo[5,1-dl-1,2,3,5-tetrazin-4-one,
  3-(2-bromoethyl)-8-carbamoyl-[3H]-imidazo-5,1-d]-1,2,3,5-tetrazin-4-one,
  3-benzyl-8-carbamoyl-[3H]-imidazo[5,1-d]-1,2,3,5-tetrazin-4-one, 8-carbamoyl-3-(2-methoxyethyl)-[3H]-imidazo[5,1-d]-1,2,3,5-tetrazin-4-one, 8-carbamoyl-3-cyclohexyl-[3H]-imidazo[5,1-d]-1,2,3,5-tetrazin-4-one, and 8-carbamoyl-3-(methoxybenzyl)-[3H]imidazo[5,1-d]-1,2,3,5-tetrazin-4-one.

Methods of making the [3H]-imidazo[5,1-d]-1,2,3,5-tetrazin-4-one derivatives described above are disclosed in U.S. Pat. No. 5,260,291, the contents of which are incorporated herein by reference in their entirety. In addition, for methods of making temozolomide in particular, Stevens et al., J. Med. Chem, 27, 196-201 (1984) may be consulted; the contents of this publication are incorporated herein by reference in their entirety.

In some embodiments where the compound of Formula A, and particularly Formula 1, is administered with temozolomide, the compound of Formula A and temozolomide may be administered for the treatment of adult patients with newly diagnosed glioblastoma multiforme concomitantly with radiotherapy and then maintenance treatment with temozolomide, and optionally the compound of Formula A, may take place. In such embodiments, temozolomide may be administered at 75 mg/m$^2$ for 42 days concomitant with focal radiotherapy (e.g., 60 Gy administered in 30 fractions) followed by an initial maintenance dose of 150 mg/m$^2$ once daily for Days 1-5 of a 28-day cycle of temozolomide for 6 cycles.

In some embodiments where the compound of Formula A, and particularly Formula 1, is administered with temozolomide, the compound of Formula A and temozolomide may be administered for the treatment of adult patients with refractory anaplastic astrocytoma, i.e., patients who have experienced disease progression on a drug regimen containing nitrosourea and procarbazine. In such embodiments, temozolomide may be administered at an initial dose of 150 mg/m$^2$ once daily for 5 consecutive days per 28-day treatment cycle.

Temozolomide may be administered in unit dosage form as, e.g., 5 mg, 20 mg, 100 mg, 140 mg, 180 mg, or 250 mg capsules or as a 100 mg powder for injection (e.g., as an intravenous infusion over 90 minutes)

For patients with newly diagnosed high grade glioma, temozolomide may be administered in the concomitant phase at 75 mg/m$^2$ daily for 42 days concomitant with focal radiotherapy (60 Gy administered in 30 fractions) followed by maintenance temozolomide for 6 cycles. For the maintenance phase, temozolomide may be administered as follows: Cycle 1: Four weeks after completing the temozolomide plus radiotherapy phase, temozolomide is administered for an additional 6 cycles of maintenance treatment. Dosage in Cycle 1 (maintenance) is 150 mg/m$^2$ once daily for 5 days followed by 23 days without treatment. Cycles 2-6: At the start of Cycle 2, the dose can be escalated to 200 mg/m$^2$, if the CTC nonhematologic toxicity for Cycle 1 is Grade less than or equal to 2 (except for alopecia, nausea, and vomiting), absolute neutrophil count (ANC) is greater than or equal to $1.5 \times 10^9$/L, and the platelet count is greater than or equal to $100 \times 10^9$/L. The dose remains at 200 mg/m$^2$ per day for the first 5 days of each subsequent cycle except if toxicity occurs. If the dose was not escalated at Cycle 2, escalation should not be done in subsequent cycles.

For adult patients with refractory anaplastic astrocytoma, the initial dose of temozolomide is 150 mg/m$^2$ once daily for 5 consecutive days per 28-day treatment cycle.

For additional guidance as to dosing of temozolomide, the prescribing information for TEMODAR® (the brand name temozolomide sold by Merck & Co., Inc.) may be consulted.

According to the invention, a compound of Formula A, and particularly Formula 1, can be administered a subject having a brain or CNS tumor or neoplasm in conjunction with administration of a one or more other agents. The agents may be administered to the subject separately or together, and by the same or different routes of administration. Where suitable, agents administered on the same schedule may be combined in the same dosage form so that they are coadministered.

In the methods of the invention, the compound of Formula A, and particularly Formula 1, can be administered by routes commonly known in the art. This includes oral administration, or any other convenient route. The compound of Formula A may also be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, transmucosal, rectally, by inhalation, or topically, particularly to the ears, nose, eyes, or skin. The mode of administration is left to the discretion of the practitioner. In most instances, administration will result in the release of a compound into the bloodstream.

In specific embodiments, it may be desirable to administer a compound locally. This may be achieved, for example, and not by way of limitation, by local infusion, topical application, by injection, by means of a catheter, by means of a suppository, or by means of an implant, said implant being of a porous, non-porous, or gelatinous material, including membranes, such as sialastic membranes, or fibers. In such instances, administration may selectively target a local tissue without substantial release of a compound into the bloodstream.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In another embodiment, a compound is delivered in a vesicle, in particular a liposome (see Langer, 1990, Science 249:1527-1533; Treat et al., in Liposomes in the Therapy of Infectious Disease and Bacterial infection, Lopez-Berestein and Fidler (eds.), Liss, New York, pp. 353-365 (1989); Lopez Berestein, ibid., pp. 317-327; see generally ibid.).

In another embodiment, a compound is delivered in a controlled release system (see, e.g., Goodson, in Medical Applications of Controlled Release, supra, vol. 2, pp. 115-138 (1984)). Examples of controlled-release systems are discussed in the review by Langer, 1990, Science 249:1527-1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105).

The present invention provides a method of treating breast cancer in a subject. The term subject, as used herein, refers to the animal being treated, wherein the animal can be a mammal such as a human.

The therapeutically effective amount of the compound of Formula A, and particularly Formula 1, is the dose of this compound, or of a pharmaceutically acceptable salt thereof, that provides a therapeutic benefit in the treatment or management of a tumor, delays or minimizes one or more symptoms associated with a tumor, or enhances the therapeutic efficacy of another therapeutic agent used in the treatment or management of a tumor. The therapeutically effective amount may be an amount that reduces or inhibits the growth of breast cancer. A person skilled in the art would recognize that the therapeutically effective amount may vary depending on known factors such as the pharmacodynamic characteristics of the particular active ingredient and its mode and route of administration; age, sex, health and weight of the recipient; nature and extent of symptoms; kind of concurrent treatment, frequency of treatment and the effect desired. A person skilled in the art would also recognize that the therapeutically effective amount, or dose, of the compound of Formula A can be determined based on the disclosures in this patent application and common knowledge in the art.

The amount of a compound, or the amount of a composition comprising a compound, that will be effective in the treatment and/or management of a tumor can be determined by standard clinical techniques. In vitro or in vivo assays may optionally be employed to help identify optimal dosage ranges.

In some cases, the dosage of a compound may be determined by extrapolating from the no-observed-adverse-effective-level (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., $mg/m^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, see Guidance for Industry Estimating the Maximum Safe Starting Dose in Initial Clinical Trials for Therapeutics in Adult Healthy Volunteers, U.S. Department of Health and Human Services Food and Drug Administration Center for Drug Evaluation and Research (CDER), Pharmacology and Toxicology, July 2005. In one embodiment, a compound or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

A dosage regime for a human subject can be extrapolated from animal model studies using the dose at which 10% of the animals die ($LD_{10}$). In general the starting dose of a Phase I clinical trial is based on preclinical testing. A standard measure of toxicity of a drug in preclinical testing is the percentage of animals that die because of treatment. It is well within the skill of the art to correlate the $LD_{10}$ in an animal study to a maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al., Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537. In certain embodiments, the adjustment for body surface area includes host factors such as, for example, surface area, weight, metabolism, tissue distribution, absorption rate, and excretion rate. In addition, the route of administration, excipient usage, and the specific disease or tumor to target are also factors to consider. In one embodiment, the standard conservative starting dose is about $1/10$ the murine $LD_{10}$, although it may be even lower if other species (i.e., dogs) were more sensitive to the compound. In other embodiments, the standard conservative starting dose is about $1/100$, $1/95$, $1/90$, $1/85$, $1/80$, $1/75$, $1/70$, $1/65$, $1/60$, $1/55$, $1/50$, $1/45$, $1/40$, $1/35$, $1/30$, $1/25$, $1/20$, $1/15$, $2/10$, $3/10$, $4/10$, or $5/10$ of the murine $LD_{10}$. In other embodiments, an starting dose amount of a compound in a human is lower than the dose extrapolated from animal model studies. In another embodiment, a starting dose amount of a compound in a human is higher than the dose extrapolated from animal model studies. It is well within the skill of the art to start doses of the active composition at relatively low levels, and increase or decrease the dosage as necessary to achieve the desired effect with minimal toxicity.

In some of the embodiments of the present invention, the compound of Formula A, and particularly Formula 1, or a pharmaceutically acceptable salt thereof, may be used at a dose of between about 0.01 mg/kg of patient body weight per day and about 10 mg/kg of patient body weight per day, and preferably between about 0.05 mg/kg of patient body weight per day and about 5 mg/kg of patient body weight per day. Accordingly, daily doses include, without limitation, 1000 mg/day, 750 mg/day, 500 mg/day, 300 mg/day, 250 mg/day, 100 mg/day, and 50 mg/day.

The compound of the present invention, and its pharmaceutically acceptable salts, may be formulated in a pharmaceutical composition. In certain embodiments provided herein, the composition may comprise said compound and a pharmaceutically acceptable carrier, excipient, or diluent. The pharmaceutical compositions provided herein can be in any form that allows for the composition to be administered to a subject, including, but not limited to a human, and formulated to be compatible with an intended route of administration.

The ingredients of compositions provided herein may be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutically acceptable carriers, excipients and diluents include those approved by a regulatory agency of the Federal or a state government or listed in the U.S. Pharmacopeia or other generally recognized pharmacopeia for use in animals, and more particularly in humans. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP) SP (XXI)/NF (XVI). In general, lactose free compositions comprise an active ingredient, a binder/filler, and a lubricant in pharmaceutically compatible and pharmaceutically acceptable amounts. Preferred lactose free dosage forms comprise a compound, microcrystalline cellulose, pre-gelatinized starch, and magnesium stearate.

Further provided herein are anhydrous pharmaceutical compositions and dosage forms comprising one or more compounds, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a therapeutically effective amount of a compound preferably in purified form, together with a suitable amount of carrier so as to provide the form for proper administration to the patient.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL® PH 101, AVICEL® PH 103 AVICEL® RC 581, AVICEL® PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL® RC 581. Suitable anhydrous or low moisture excipients or additives include AVICEL® PH 103™ and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB 0 SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A compound can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008, 719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Example 1

Penetration of the Blood-Brain Barrier

The compound of Formula I was tested to determine bioavalability in tissues of the brain and CNS.

Male CD-1 mice (N=3/group) received a single dose of lapatinib or the compound of Formula I at 100 mg/kg via oral gavage. Animals were not food fasted prior to dosing. Dose volumes were calculated based on the animals' body weights measured before the study.

Plasma and tissue samples were collected 1, 4, 8 and 24 hours post dose (4 time-points/group, and 3 animals/time-point). Whole blood samples were collected into a Na heparin containing tube. Within 30 minutes of collection, the samples were centrifuged at approximately 3,000×g for 10 minutes at 2 to 8° C. to obtain plasma. The plasma samples were divided into 2 aliquots by transferring into 2 cryogenic vials and stored in a freezer at −75±15° C. prior to analysis. Tissues were collected after the blood was collected. Tissues (brain, liver and kidneys) were washed with ice-cold PBS, and the weight was measured and recorded. Each tissue was transferred into a glass vial and stored in a freezer at −75±15° C. prior to sample analysis.

The plasma/brain concentration results are shown in FIG. 1. The compound of Formula 1 crossed the blood brain barrier and attained high concentrations in CNS and brain tissue. Following administration of Formula 1, the concentration observed in CNS tissue was substantially higher that in blood, and remained higher for the duration of the assay (at least 24 hours).

Example 2

Penetration of the Blood-Brain Barrier by Quantitative Whole Body Autoradiography The compound of Formula 1 was tested to determine bio-distribution in tissues of the brain and CNS.

Lister Hooded partially pigmented male rats (N=1 rat per time point) received a single dose of the compound of Formula 1 at 30 mg/kg body weight ($^{14}$C labeled, 3.7 MBq/kg body weight) via oral gavage. Animals were not fasted prior to dosing.

Six rats (age 8-10 weeks old) were administered a single oral dose of [$^{14}$C]-labeled Formula 1; total dose of 30 mg/kg and a total radioactivity dose of 3.7 MBq/kg (100 µCi/kg). One rat/time point was euthanized by $CO_2$ overdose at each of the following times after dose administration: 1, 6, 24, 72, 120 and 168 hours, followed by immediate snap freezing in hexane/solid $CO_2$, subsequent freezing at −20° C., followed by whole-body autoradiography.

It is noteworthy that concentrations of radioactivity in brain were comparable to that in blood at 6 and 24 hours after dosing, indicating good penetration of the blood brain barrier by the compound of Formula I.

Example 3

Efficacy Alone or in Combination with Irradiation in an Intracranial Glioma Model in Mice The compound of Formula 1 was tested to determine antitumor effects when tumors are growing in the brain.

GL261-luc2 luciferase expressing cells were implanted intracranially (2 mm right lateral and 1 mm anterior from Bregma, 2-3 mm down from burr hole) into C57BL/6 albino female mice (N=14 per treatment group). Beginning 8 days after cell injection, mice received vehicle or the compound of Formula I at 70 mg/kg body weight (once daily, 5 days on/2 days off schedule) via oral gavage, with or without head-only irradiation (once daily for 5 days). Tumor burden in the brain was evaluated utilizing bioluminescence.

Figure 2:
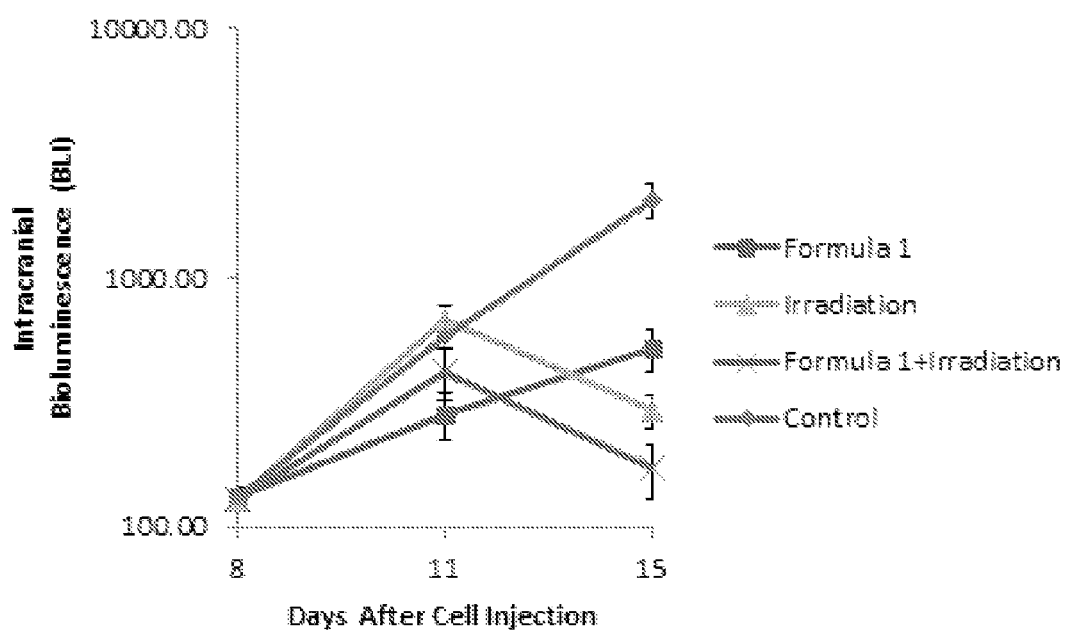
FIG. 2 shows the evaluation using bioluminescence of tumor burden in the brain of mice after cell (GL261-luc2) injection, for mice receiving the N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine with or without head-only irradiation.

As seen in FIG. 2, the compound of Formula 1 reduced the growth of glioma tumors in the brain, and increased the anti-tumor effects of irradiation on tumors in the brain (mean+/−SEM plotted).

I claim:

1. A method for treating a brain or central nervous system tumor comprising administering to a subject in need of such treatment a therapeutically effective amount of a compound of Formula A:

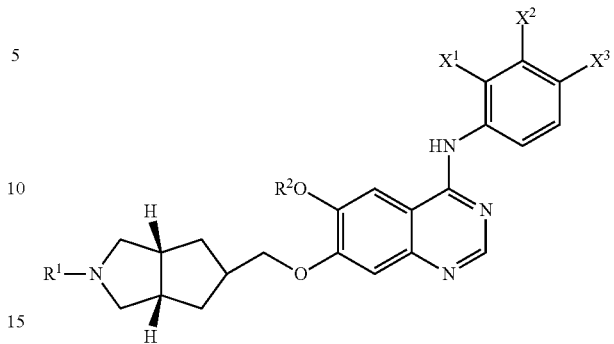

Formula A wherein
each of $X^1$, $X^2$ and $X^3$ are independently selected from the group consisting of H, F and Cl, wherein at least two of $X^1$, $X^2$ and $X^3$ are F or Cl;
$R^1$ is $C_1$ to $C_3$ alkyl; and $R^2$ is $C_1$ to $C_3$ alkyl;
or a pharmaceutically acceptable salt thereof.

2. The method according to claim 1, comprising administering to a subject in need of such treatment a therapeutically effective amount of a compound of Formula I:

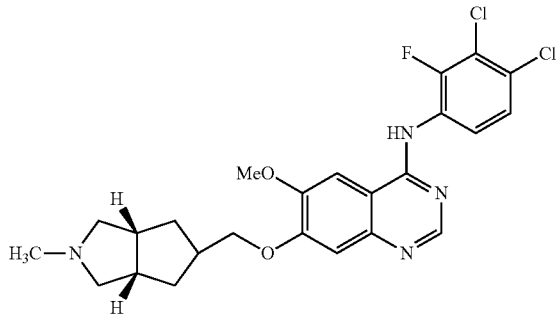

Formula 1 or a pharmaceutically acceptable salt thereof.

* * * * *